United States Patent
Cooker et al.

(10) Patent No.: US 7,232,783 B2
(45) Date of Patent: Jun. 19, 2007

(54) PROPYLENE OXIDE CATALYST AND USE

(75) Inventors: Bernard Cooker, Malvern, PA (US); Roger A. Grey, West Chester, PA (US); Edrick Morales, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 124 days.

(21) Appl. No.: 11/173,350

(22) Filed: Jul. 2, 2005

(65) Prior Publication Data

US 2007/0004583 A1   Jan. 4, 2007

(51) Int. Cl.
*B01J 21/00* (2006.01)
(52) U.S. Cl. .......................... 502/60; 502/63; 502/70; 502/74
(58) Field of Classification Search .................. 502/73, 502/74, 77, 60, 63
See application file for complete search history.

(56) References Cited

U.S. PATENT DOCUMENTS

| 4,410,501 | A | 10/1983 | Taramasso et al. | 423/326 |
| 6,972,337 | B1* | 12/2005 | Onimus et al. | 549/533 |
| 6,984,606 | B2* | 1/2006 | Dessau | 502/242 |
| 2005/0282699 | A1* | 12/2005 | Grey | 502/66 |

FOREIGN PATENT DOCUMENTS

| BE | 1001038 A7 | 6/1989 |
| JP | 4-352771 | 12/1992 |

* cited by examiner

*Primary Examiner*—Elizabeth D. Wood
(74) *Attorney, Agent, or Firm*—William C. Long

(57) ABSTRACT

A process is provided for the production of a noble metal on TS-1 catalyst useful for the production of propylene oxide wherein TS-1 from hydrothermal crystallization has noble metal dispersed thereon, the resulting material is spray dried and template used in the crystallization is removed, the resulting product is treated with hydrogen to form active catalyst for propylene oxide production.

11 Claims, No Drawings

PROPYLENE OXIDE CATALYST AND USE

FIELD OF THE INVENTION

The present invention relates to a propylene oxide catalyst comprised of TS-1, and to the catalyst preparation and use.

DESCRIPTION OF THE PRIOR ART

The use of catalyst comprised of TS-1 in the production of propylene oxide has long been known. See, for example, U.S. Pat. No. 4,410,501. Usually the reaction system was comprised of methanol and water, and hydrogen peroxide was the propylene oxidant.

It was further discovered that propylene oxide can be formed by reaction of hydrogen, oxygen and propylene over a catalyst comprised of a noble metal such as palladium supported on TS-1. See, for example, Japanese Kokai No. 4-352771.

The preparation of a noble metal on TS-1 catalyst has, however, been a challenging task generally involving a large number of separate steps thus making the catalyst both difficult and expensive to produce.

In accordance with the present invention a greatly simplified process is presented for the production of a catalyst comprised of noble metal supported on TS-1 which is especially useful for the production of propylene oxide.

BRIEF DESCRIPTION OF THE INVENTION

In accordance with the present invention a noble metal is deposited on wet TS-1 crystals containing associated template from the crystal-forming reaction. In one such method the wet TS-1 crystals are combined with a noble metal source such as tetramine palladium chloride, tetramine palladium nitrate, or the like and the palladium is allowed to ion exchange onto the TS-1. Other deposition methods can be used. Following noble metal deposition, the noble metal containing TS-1 is spray dried to produce particulate solid which retains template from the crystallization. Organic template is removed from the particulate spray dried product such as by calcination in the presence of oxygen. Other template removal methods can be used including pyrolysis with an inert, and the like. During any calcination in the presence of oxygen, the oxygen level is maintained outside flammable limits as by addition of inert gas. After template removal the noble metal containing TS-1 is treated with hydrogen to produce catalyst which has high selectivity and activity for the reaction of propylene, oxygen and hydrogen to form propylene oxide. A substantial number of variations are possible to the above described process as will be explained hereinafter.

DETAILED DESCRIPTION

In practice of the invention, TS-1 is prepared by hydrothermal crystallization of a source of titanium such as tetraethyl orthotitanate, a source of silicon such as tetraethyl orthosilicate and a template such as tetrapropyl ammonium hydroxide. Water is also provided. In general, the various known methods for the preparation of TS-1 by hydrothemal crystallization can be employed.

It is essential in practice of the invention that the recovered wet TS-1 crystals containing associated template be spray dried. Where a binder such as silica, alumina, kaolin, silica alumina and the like is to be incorporated with the final catalyst, a source of binder such as colloidal silica is mixed with water, preferably deionized water, and the pH adjusted to the region of about 8 to 10, preferably 9.0 to 9.5, as by addition of ammonia, and the wet TS-1 from TS-1 preparation solids separation is added to the silica water admixture.

Where the ultimate catalyst is to be used to produce propylene oxide by reaction of propylene, oxygen and hydrogen, a noble metal source such as tetraammine palladium nitrate or the like is incorporated with the TS-1, preferably by an ion exchange procedure.

The slurry comprised of the above components is adjusted to provide an appropriate solids concentration, e.g. 15-40 wt % and the slurry can be screened to ensure that particles of excessive size are separated. The resulting slurry is spray dried to a dry particulate product having 5-80, preferably, 15 to 35 micron average diameter.

The spray dried product is treated to remove template as by calcination in an oxygen-containing atmosphere such as air at 300-800° C. preferably at 450-650° C., whereby the organic template is essentially removed from the noble metal containing TS-1.

Finally, the spray dried product from which template has been removed is treated such as at reducing conditions with hydrogen at 30-500° C., preferably 50-150° C. to convert the noble metal to reduced active form for use in propylene oxide production. Alternatively other reducing agents such as methanol can be used or the catalyst can be reduced in situ during the reaction of hydrogen, oxygen and propylene to form propylene oxide.

In summary, the preferred sequence of steps for the formation of the active catalyst is as follows:

1. TS-1 crystals are prepared by hydrothermal crystallization using an organic template such as a tetrapropyl ammonium hydroxide.
2. A binder such as silica dispersed in water, e.g. colloidal silica, is combined with the wet template-containing TS-1 and a noble metal ion is dispersed onto the TS-1 as by ion exchange. Optionally, the noble metal deposition can be carried out before TS-1 is admixed with the binder to avoid deposition of noble metal on the binder or noble metal can be added to the binder before mixing with TS-1. It is also possible to carryout the noble metal addition after spray drying although this is less preferable.
3. The resulting dispersion is spray dried to produce a 5-80 micron particle size dry product.
4. The spray dried product is calcined or pyrolyzed, preferably in an oxygen containing atmosphere, at 300-800° C., preferably 400-600° C. to remove template and secure noble metal dispersion on the TS-1.
5. The calcined solids are heated at 30-500° C., preferably 50-150° C. under a hydrogen containing atmosphere to convert the noble metal to active form and the resulting product is recovered and can be directly used in the production of propylene oxide.

A. Hydrothemal Crystallization

The preparation of TS-1 by hydrothemal crystallization is by now well known and the preparation techniques previously used can be employed in practice of this invention.

Titanium zeolite synthesis typically comprises reacting a titanium compound, a silicon source, and a templating agent at a temperature and for a time sufficient to form a titanium zeolite. Suitable titanium compounds useful in titanium zeolite synthesis include, but are not limited to, titanium alkoxides and titanium halides as well as mixtures. Preferred titanium alkoxides are titanium tetraisopropoxide, titanium tetraethoxide and titanium tetrabutoxide. Titanium tetraethoxide is especially preferred. Preferred titanium halides include titanium trichloride and titanium tetrachloride.

Suitable silicon sources include, but are not limited to, colloidal silica, fumed silica and silicon alkoxides. Preferred silicon alkoxides are tetraethylorthosilicate, tetramethylorthosilicate, and the like. Tetraethylorthosilicate is especially preferred.

The templating agent used in crystal synthesis is typically a tetraalkylammonium cation, particularly tetrapropylammonium cation. The templating agent is typically used in the zeolite synthesis as a templating agent compound consisting of the templating agent and an anionic species. The tetraalkylammonium cation is typically used as a hydroxide, halide, nitrate, acetate, and the like compound. Tetraalkylammonium hydroxides and tetraalkylammonium halides, such as tetrapropylammonium hydroxide tetrapropylammonium halide, are preferred templating agent compounds. Tetrapropylammonium hydroxide is especially preferred.

Synthesis of titanium zeolites is carried out by a hydrothermal crystallization of a reaction mixture prepared by combining the titanium compound, silicon source, and templating agent compound in the presence of water.

Generally, the hydrothermal process used to prepare titanium zeolites involves forming a reaction mixture wherein the molar ratios of additives (as defined in terms of moles of templating agent, moles of $SiO_2$ and moles of $TiO_2$) comprise the following molar ratios: $TiO_2$:$SiO_2$=0.5-5:100; and templating agent: $SiO_2$=10-50:100. The water: $SiO_2$ molar ratio is typically from about 1000-5000:100 and the solvent: $SiO_2$ molar ratio may be in the range of 0-500:100.

The reaction mixture is prepared by mixing the desired sources of titanium, silicon and templating agent compound to give the reaction mixture. It is also typically necessary that the mixture have a pH of about 9 to about 13. The basicity of the mixture is controlled by the amount of templating agent compound (if it is in the hydroxide form) which is added and the use of other basic compounds. To increase the basicity of the mixture, more templating agent (hydroxide) compound is typically added to the reaction mixture. If another basic compound is used, the basic compound is preferably an organic base that is free of alkali metals, alkaline earth metals, and the like. The addition of other basic compounds may be needed if the templating agent is added as a salt, e.g., halide or nitrate. Examples of these basic compounds include ammonium hydroxide, quaternary ammonium hydroxides and amines. Specific examples include tetraethylammonium hydroxide, tetrabutylammonium hydroxide, n-butylamine, and tripropylamine.

After the reaction mixture is formed, it is reacted at a temperature and a time sufficient to form a molecular sieve. Typically, the reaction mixture is heated at a temperature of about 100° C. to about 250° C. for a period of about 0.5 hours to about 96 hours in a sealed vessel under autogenous pressure. Preferably, the reaction mixture is heated at a temperature range from about 125° C. to about 200° C., most preferably from about 150° C. to about 180° C. After the desired reaction time, the titanium zeolite is recovered.

Suitable zeolite recovery methods include filtration and washing (typically with deionized water), rotary evaporation, centrifugation, and the like.

The titanium zeolite useful in the invention preferably is of the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 may be used in the process of invention.

B. Binder Dispersion Preparation

A binder such as silica, alumina, silica-alumina, kaolin, zeolites, silicic acid, silicates, phosphates and the like is preferably incorporated in the final catalyst.

For example, the TS-1 can be dispersed in water and ground to the desired particle size e.g. 2 microns or less. A colloidal suspension of binder such as silica can then be added to the TS-1 dispersion and the resulting admixture spray dried.

C. Noble Metal Deposition

A critical feature of the finished catalyst is the presence of noble metal dispersed thereon. Without the noble metal, the catalyst is not effective for the production of propylene oxide through reaction of oxygen, hydrogen and propylene.

Although the noble metal can be dispersed on the binder or on the admixture of TS-1 and binder, better results are achieved where the noble metal is combined with the TS-1 before admixture with binder.

The noble metal source comprises a compound or complex of palladium, platinum, gold, silver, iridium, rhenium, ruthenium, osmium, nickel, or mixtures thereof. Palladium, platinum, and gold are particularly desirable; palladium is most preferred. There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals, as well as compounds containing a mixture of such ligands.

The typical amount of noble metal present in the noble metal-containing titanium zeolite will be in the range of from about 0.001 to 10 weight percent. The noble metal is suitably incorporated into the zeolite by ion-exchange with, for example, a tetraammine palladium salt such as tetraammine palladium dinitrate, dihalide or sulfate.

Generally, the wet TS-1 crystals containing template are contacted with an aqueous solution containing the noble metal compound or complex at 20-100° C. for a sufficient time to ion exchange the noble metal onto the TS-1, generally 5 minutes to 2 hours or more. It is advantageous to adjust the pH of the mixture of TS-1 and noble metal compound solution to 7.0-10.0 or thereabouts by ammonia addition, to complete noble metal transfer.

The noble metal component can be dispersed onto the TS-1 either before or after the TS-1 has been combined with binder or the noble metal added to the binder dispersion before the dispersion is combined with the TS-1.

D. Spray Dry Feed Preparation

Following addition of the noble metal, a feed to the spray drying step is formed. A dispersion comprised of the binder, if any, and the TS-1 having dispersed thereon noble metal in water is adjusted to an appropriate solids content, preferably 10 to 40 wt %.

If necessary the solids in the dispersion are ground to an appropriate spray drying particle size, illustratively less than 2 microns.

E. Spray Drying

The above dispersion is spray dried in order to produce a dry particulate product. A preferred procedure for carrying out spray drying is described in application Ser. No. 10/769,359 filed Jan. 30, 2004 the disclosure of which is incorporated herein by reference. The spray drying results in a product having 5-80, preferably 25 to 35 micron diameter on the average, air feed temperature to spray drying is 400-1000° F., preferably 500-850° F., air exit temperature is 180-240° F., preferably 195-210° F.

F. Calcination

The spray dried catalyst solid can be calcined under an oxygen-containing atmosphere usually containing 8 vol % oxygen or less in an inert such as nitrogen in accordance with generally known procedures. Preferably air diluted with inert such as nitrogen is used. In most preferred practice a rotary kiln is employed and the calcination is carried out for a time sufficient to remove the template and disperse the noble metal on the TS-1. During calcination, gas flow is countercurrent to the catalyst, both solids and gas flows are continuous. Other procedures including use of a belt roaster, fixed or fluidized bed, and other procedures can be used. Calcination times of up to about 4-6 hours are suitable to remove the template.

G. Hydrogen Treatment

From the calcination kiln the calcined solids are transferred to a second heat treatment zone, preferably a second rotary kiln, wherein the catalyst is contacted at 30-500° C. with a hydrogen containing atmosphere. In this second kiln both solids and gas are fed continuously with solids from the first kiln flowing directly to the second kiln to conserve heat, minimize size of the second kiln and minimize reheat duty. Preferably 2-20% by volume hydrogen in inert such as nitrogen is used and the treatment is for up to 5 hours or so.

Fixed bed procedures can be used in both the template removing calcination and the hydrogen treatment. In such procedures, both of the procedures can be accomplished by appropriate adjustment of gases fed to the fixed bed treatment zone.

The hydrogen heat treatment serves to improve performance of the catalyst in the production of propylene oxide.

Advantages of the present invention process reside in that the process can be operated continuously with but a single calcination step and results in the production of a highly active and selective catalyst.

The catalyst prepared as above indicated is useful in the production of propylene oxide by reaction of propylene oxygen and hydrogen. Generally known conditions are employed for this reaction. The epoxidation is carried out in the liquid phase, and it is advantageous to work at elevated pressure of 1-100 bars gauge. Suitable solvents used in catalyst preparation and in the epoxidation include, but are not limited to, lower aliphatic alcohols such as methanol, ethanol, isopropanol, and tert-butanol, or 35 mixtures thereof, and water. Fluorinated alcohols can be used. It is also possible to use mixtures of the cited alcohols with water. Methanol and methanol/water are preferred. Supercritical carbon dioxide solvent can also be used. Additional solvent can be added before or during epoxidation to improve process results.

Epoxidation according to the invention is carried out at a temperature effective to achieve the desired propylene epoxidation, preferably at temperatures in the range of 0-125° C., more preferably 20-80° C. The reaction is carried out at elevated pressures not to exceed about 100 bars gauge, preferably in the range 2-80 bars gauge.

As the carrier gas, inert gases such as helium, neon, argon, krypton and xenon are suitable as well as nitrogen and carbon dioxide. Saturated hydrocarbons with 1-8, especially 1-6, and preferably with 1-4 carbon atoms, e.g., methane, ethane, propane and n-butane, are also suitable. Nitrogen and saturated $C_1$-$C_4$ hydrocarbons are the preferred carrier gases. Mixtures of the listed carrier gases can also be used.

The molar ratio of hydrogen to oxygen can usually be varied in the range of $H_2$:$O_2$-1:10 to 5:1 and is especially favorable at 1:5 to 1:1. The molar ratio of oxygen to olefin can be 3:1 or more but preferably is 1:1 to 1:20, and most preferably 1:1.5 to 1:10.

The following example is illustrative of a practice of the process of the invention.

A. Hydrothermal Crystallization

Water, tetraethylortho silicate, tetrapropylammonium hydroxide and titanium isopropoxide are mixed in a batch autoclave for 1 hour at 25 C. The mixture is heated, under autogenous pressure, with continuous agitation, at the rate of 1° C./min to 185° C. and held for 24 hours. The resulting TS-1 crystal slurry is filtered and a cake with 50 wt % moisture is obtained. The cake is washed with de-ionized water. It is then transferred to Step B below.

B. Noble Metal Deposition

The wet cake from Step A is charged to a mixing tank containing de-ionized water under sustained agitation to completely disperse the TS-1 crystals. This takes approximately 20 to 60 minutes. The pH is measured and adjusted with aqueous ammonia to a value of 9.5. The typical pH of TS-1 wet cake with tetrapropylammonium template in water is approximately 9. Aqueous tetraammine palladium nitrate is added to the mixing tank and the contents are agitated for 30 minutes while monitoring the pH. Sufficient tetraammine palladium nitrate is used to provide 0.1 wt % Pd on the TS-1. The TS-1 crystal slurry is transferred to Step C.

C. Spray Dryer Feed Preparation

Colloidal silica is charged to the mixing tank containing the TS-1 crystal slurry from Step B above. An in-line grinder is used to grind clumps in the slurry for 20 to 30 minutes. The dispersion, comprising 20 wt % solids, is transferred to Step D.

D. Spray Drying

The dispersion is spray dried at an air feed temperature of 320° C. and an air exit temperature of 100° C. The product particles have a volume-weighed median diameter of 30 microns.

E. Oxidative Calcination

The dryer product is fed to a kiln, with countercurrent flow of 8 vol % oxygen in nitrogen. The peak material temperature is 550° C. and the catalyst is between 520 and 550° C. for 30 minutes in the rotary kiln.

F. Hydrogen Treatment

From the oxidative kiln, the calcined solids pass to a second kiln, which operates at a peak material temperature of 100° C., with continuous counter-current flow of 4% hydrogen in nitrogen. The catalyst in the kiln is at 90 to 100° C. for 30 minutes. The catalyst discharges to a product receiver.

The Pd TS-1 catalyst prepared as above described is an excellent catalyst for production of propylene oxide by reaction of propylene, oxygen and hydrogen.

In a specific practice, the catalyst prepared as above is slurried in a mixture of methanol and water, the solids concentration is 5 wt %. Phosphate buffer is added to maintain pH at 6.5.

A feed gas mixture comprised by volume of 3% propylene, 4.8% oxygen, 1.7% hydrogen and the remainder ballast gas is reacted at 50° C. and 340 psig.

A yield of propylene oxide plus propylene oxide equivalents of 90% based on propylene converted was achieved.

We claim:

1. A process for the formation of catalyst for propylene oxide production which comprises:
   a) forming TS-1 crystals by hydrothermal crystallization in the presence of an organic template,
   b) recovering template containing TS-1 crystals from the hydrothermal crystallization,
   c) incorporating noble metal with the recovered TS-1 crystals before or after spray drying step d),
   d) spray drying the noble metal containing TS-1 to form particulate solids,
   e) removing template from the spray dried particulate solids, and
   f) reducing the particulate solids from which template has been removed to form active catalyst for propylene oxide production.

2. The process of claim 1 wherein a binder is incorporated with the TS-1 crystals recovered from step b) before deposition of the noble metal.

3. The process of claim 1 wherein a binder is incorporated with the TS-1 crystals recovered from step b) after deposition of the noble metal on the TS-1 crystals.

4. The process of claim 1 wherein noble metal deposition takes place after spray drying step d).

5. The process of claim 1 wherein a colloidal silica binder is incorporated with the TS-1 crystals recovered from step b).

6. The process of claim 1 wherein step f) is carried out by treatment with hydrogen.

7. The process of claim 1 wherein the template is tetrapropylammonium hydroxide.

8. The process of claim 1 wherein the noble metal is palladium.

9. The process of claim 1 wherein the noble metal is deposited by ion exchange in step c).

10. The process of claim 1 wherein template is removed by oxidative calcination.

11. The process of claim 1 wherein a binder having noble metal dispersed thereon is incorporated with the TS-1 crystals.

* * * * *